(12) United States Patent
Minty et al.

(10) Patent No.: US 11,708,464 B2
(45) Date of Patent: Jul. 25, 2023

(54) POLY (AMINO ACID) RHEOLOGY MODIFIER COMPOSITIONS AND METHODS OF USE

(71) Applicant: Ecovia Renewables Inc., Ann Arbor, MI (US)

(72) Inventors: Jeremy J. Minty, Ann Arbor, MI (US); Samuel Kohley, Ann Arbor, MI (US); Daniel Lee, Arlington, VA (US); Harry Poppick, Ann Arbor, MI (US)

(73) Assignee: Ecovia Renewables Inc., Ann Arbor, MI (US)

( * ) Notice: Subject to any disclaimer, the term of this patent is extended or adjusted under 35 U.S.C. 154(b) by 344 days.

(21) Appl. No.: 16/616,815

(22) PCT Filed: May 25, 2018

(86) PCT No.: PCT/US2018/034678
§ 371 (c)(1),
(2) Date: Nov. 25, 2019

(87) PCT Pub. No.: WO2018/222545
PCT Pub. Date: Dec. 6, 2018

(65) Prior Publication Data
US 2020/0095386 A1  Mar. 26, 2020
US 2021/0040275 A9  Feb. 11, 2021

Related U.S. Application Data

(60) Provisional application No. 62/511,994, filed on May 27, 2017.

(51) Int. Cl.
| C08J 3/12 | (2006.01) |
| C08J 3/24 | (2006.01) |
| A23L 29/20 | (2016.01) |
| C09D 7/43 | (2018.01) |
| C09K 8/68 | (2006.01) |
| C09K 8/70 | (2006.01) |
| A61K 8/02 | (2006.01) |
| A61K 47/42 | (2017.01) |
| C04B 16/04 | (2006.01) |
| C04B 24/12 | (2006.01) |
| C09D 11/04 | (2006.01) |
| C04B 24/26 | (2006.01) |
| C11D 3/37 | (2006.01) |
| A61K 8/88 | (2006.01) |
| C09K 8/035 | (2006.01) |
| A01N 25/00 | (2006.01) |
| A61Q 19/00 | (2006.01) |
| C04B 103/00 | (2006.01) |

(52) U.S. Cl.
CPC ............. *C08J 3/124* (2013.01); *A01N 25/00* (2013.01); *A23L 29/20* (2016.08); *A61K 8/0241* (2013.01); *A61K 8/88* (2013.01); *A61K 47/42* (2013.01); *A61Q 19/00* (2013.01); *C04B 16/04* (2013.01); *C04B 24/12* (2013.01); *C04B 24/2652* (2013.01); *C08J 3/24* (2013.01); *C09D 7/43* (2018.01); *C09D 11/04* (2013.01); *C09K 8/035* (2013.01); *C09K 8/685* (2013.01); *C09K 8/70* (2013.01); *C11D 3/3719* (2013.01); *A23V 2002/00* (2013.01); *A61K 2800/10* (2013.01); *A61K 2800/41* (2013.01); *A61K 2800/48* (2013.01); *A61K 2800/546* (2013.01); *C04B 2103/0079* (2013.01); *C08J 2377/04* (2013.01)

(58) Field of Classification Search
CPC . C08J 3/124; C08J 3/24; C08J 2377/04; C08J 29/20; C08J 7/43; C08J 11/04; C08J 8/685; C08J 8/70; C08J 8/035; C08J 8/0241; C08J 47/42; C08J 8/88; C08J 2800/10; C08J 2800/48; C08J 2800/546; C08J 2800/41; C08J 16/04; C08J 24/12; C08J 24/2654; C08J 2103/0079; C08J 3/3719; C08J 25/00; C08J 19/00; C08J 2002/00
See application file for complete search history.

(56) References Cited

U.S. PATENT DOCUMENTS

| 5,955,549 A | 9/1999 | Chang |
| 7,364,879 B2 | 4/2008 | Ho et al. |

(Continued)

FOREIGN PATENT DOCUMENTS

| CN | 1324143 C | 7/2007 |
| CN | 101048133 A | 10/2007 |

(Continued)

OTHER PUBLICATIONS

Machine English translation of CN 105733250, Chen et al., Jul. 6, 2016.*

(Continued)

*Primary Examiner* — Patrick D Niland
(74) *Attorney, Agent, or Firm* — Honigman LLP

(57) ABSTRACT

Rheology modifiers comprising cross-linked poly(amino acid) and methods of their use in aqueous compositions. The modifiers comprise cross-linked poly(amino acid) microparticles having a mean equivalent diameter when fully swollen in deionized water of up to 1000 μm, as measured by laser diffraction. In particular, the poly(amino acid) is D-, L- or D,L-γ-poly(glutamic acid). A method of preparing the modifier comprises cross-linking a poly(amino acid), drying the cross-linked poly(amino acid) and grinding the cross-linked poly(amino acid) to have the required diameter.

5 Claims, 4 Drawing Sheets

(56) References Cited

U.S. PATENT DOCUMENTS 7,759,088 B2 7/2010 Ho et al.
7,790,417 B2 9/2010 Ho et al.

FOREIGN PATENT DOCUMENTS

| CN | 101321806 A | 12/2008 |
|---|---|---|
| CN | 1803124 B | 4/2010 |
| CN | 105255173 A | 1/2016 |
| CN | 165733250 A | 7/2016 |
| EP | 1563831 A1 | 8/2005 |
| EP | 1550469 B1 | 11/2006 |
| EP | 1690525 B1 | 11/2016 |
| FR | 2874174 A1 | 2/2006 |
| JP | H11343339 A | 12/1999 |
| JP | 4015988 B2 | 11/2007 |
| JP | 4137062 B2 | 8/2008 |
| JP | 2009120585 A | 6/2009 |
| JP | 2010150148 A | 7/2010 |
| JP | 2016121187 A | 7/2016 |
| WO | 2009147951 A1 | 12/2009 |

OTHER PUBLICATIONS

Hatsuratsu KK, JP2016-121187A, Database WPI Week 201649, Thomson Scientific, Jul. 7, 2016, pp. 2, Abtract Only.
Shandong Acad Pharm Sci, CN105733250A, Database WPI Week 201671, Thomson Scientific. Jul. 6, 2016. pp. 2 Abtract Only.
Toyobo KK, JP2009-120585A, Database WPI Week 200938, Thomson Scientific, Jun. 4. 2009, pp. 3,ABTRACT Only.
Toyobo KK, JP2010-150148A. Database WPI Week 201047, Thomson Scientific, Jul. 8, 2010, pp. 3, Abtract Only.
International Search Report and Written Opinion for PCT/US2018/034678, dated Sep. 5, 2018, 23 pages.

\* cited by examiner

POLY (AMINO ACID) RHEOLOGY MODIFIER COMPOSITIONS AND METHODS OF USE

STATEMENT REGARDING FEDERALLY SPONSORED RESEARCH OR DEVELOPMENT

This invention was made with government support under the National Institute of Food and Agriculture grant 2015-33610-23476 awarded by the United States Department of Agriculture. The government of the United States of America has certain rights in the invention.

CROSS-REFERENCE TO RELATED APPLICATION

This application is a 35 U.S.C. § 371 United States National Phase Application of, and claims priority to PCT Application No. PCT/US2018/034678, filed May 25, 2018, which claims priority to U.S. Provisional Application No. 62/511,994, filed May 27, 2017. The entire contents of the aforementioned disclosures are incorporated herein by reference.

FIELD OF THE INVENTION

The present invention relates to rheology modifiers for aqueous formulations.

BACKGROUND

This section provides information helpful in understanding the invention but that is not necessarily prior art.

Rheology modifiers, also commonly known as thickeners or viscosifiers, are used in many aqueous systems and formulations, such as personal care and pharmaceutical formulations, paints and inks, coatings, foods, concrete and cement, and drilling fluids, among many other applications. Rheology modifiers for aqueous systems are generally polymeric water-soluble or water-dispersible agents that thicken aqueous systems when dissolved or that are insoluble microscopic polymer particles that thicken by swelling when dispersed in aqueous systems.

Carboxyl-containing polymers, including those produced by free-radical or addition polymerization of ethylenically unsaturated monomers (such as acrylic monomers), are among the most commonly used rheology modifiers today and have enjoyed great commercial success due to their performance and low cost. However, the thickening potency of these materials is generally limited and may be adversely affected by an aqueous matrix composition; particularly, thickening potency is often reduced in the presence of electrolytes, especially polyvalent metal cations such as $Ca^{2+}$ and $Mg^{2+}$. These issues pose important practical limitations in terms of the rheology modifier concentration needed to achieve a target viscosity range and impose restrictions on other formulation ingredients and uses.

Furthermore, polymers based on ethylenically unsaturated monomers are typically produced via regulated processes from non-renewable fossil resources and are not readily biodegradable. Motivated by environmental concerns about the production and disposal of these polymers and consumer concerns and perceptions about the use of these polymers in applications involving contact with food, topical applications, and indirect skin contact applications, there have been efforts to develop alternative thickening chemistries and materials based on non-toxic, biodegradable biopolymers. Such biopolymer thickeners are most often based on cross-linked or derivatized polysaccharides, such as starches or vegetable gums. However, these biopolymer thickeners typically have reduced thickening performance and other undesirable properties (such as unpleasant, sticky skin feel) compared to synthetic carboxyl-containing polymers based on ethylenically unsaturated monomers, and in some cases these biopolymer thickeners have a far greater cost of production (as exemplified by hyaluronic acid polymers).

There is thus a need to produce biobased, non-toxic, and biodegradable thickeners that can offer performance parity with conventional synthetic carboxyl-containing polymers based on ethylenically unsaturated monomers. Biobased, non-toxic, and biodegradable thickeners that can exceed the performance of synthetic carboxyl-containing polymers would be of particularly great value.

SUMMARY

The present disclosure provides biobased, non-toxic, and biodegradable thickeners that offer performance parity with or exceed the performance of synthetic carboxyl-containing polymers.

In a first aspect, the present invention provides rheology modifier compositions comprising cross-linked poly(amino acid) (PAA) particles, which may be of any geometric shape, having a mean equivalent spherical diameter (that is, diameter of a sphere equivalent to the mean volume of the particles) when fully swollen in deionized water of up to about 1000 μm (measured by laser diffraction). The cross-linked poly(amino acid) particles are comprised of linear polymers with amino acid monomer units that include one or more carboxylic acid side groups that are covalently cross-linked to one another. The poly(amino acids) can be obtained from a bio-based source or prepared from bio-based amino acids and are biodegradable.

In a first embodiment of the first aspect, the cross-linked poly(amino acid) (PAA) particles may be prepared from a PAA homopolymer, a copolymer of at least one amino acid that polymerizes to form monomer units that include one or more carboxylic acid side groups and at least one comonomer, or a polymer blend in which at least one polymer has amino acid monomer units that include one or more carboxylic acid side groups. In a second embodiment of the first aspect, polyglutamic acid is used to make the cross-linked poly(amino acid) particles. The polyglutamic acid that is crosslinked may be α-polyglutamic acid or γ-polyglutamic acid or a mixture of α-polyglutamic acid and γ-polyglutamic acid, and it may be a single D or L enantiomer or a mixture of D and L enantiomers of polyglutamic acid. In a third embodiment of the first aspect, a poly(amino acid) having a weight average molecular weight of from about 1000 to about 30,000,000 Daltons is used to make the cross-linked poly(amino acid) particles. In a fourth embodiment, the cross-link density of the cross-linked poly(amino acid) particles is from one bond per 10 monomer units to one bond per about 100,000 monomer units. In a fifth embodiment, the cross-linked poly(amino acid) particles have a free swelling absorbency of from about 10 to about 10,000 g water/g PAA. In a sixth embodiment, the poly(amino acid) is of biologic or synthetic origin or the PAA is made from renewable starting materials, as determined by Carbon-14/Carbon-13 isotope ratio analysis through the ASTM D6866 test method.

In a second aspect of the invention, a method of preparing a rheology modifier for an aqueous composition comprises cross-linking one of: a homopolymer of an amino acid that polymerizes to form monomer units that include at least one carboxylic acid side group, a copolymer of at least one amino acid that polymerizes to form monomer units that include one or more carboxylic acid side groups and at least one different comonomer, a combination of such homopolymers or copolymers or both, or a polymer blend in which at least one polymer has amino acid monomer units that include one or more carboxylic acid side groups to form a cross-linked poly(amino acid); and, if necessary, reducing the particle size of the cross-linked poly(amino acid) to a particle size that, when fully swollen in deionized water, will have a mean equivalent diameter of up to about 1000 µm. It is necessary to reduce the particle size of the cross-linked poly(amino acid) if, when the unreduced particle size is fully swollen in deionized water, it has a mean equivalent diameter of greater than about 1000 µm. If the cross-linked poly(amino acid) is formed as a dispersion, then the cross-linked poly(amino acid) may be isolated before reducing the particle size. Alternatively, the particle size of the cross-linked poly(amino acid) may be reduced while dispersed in an aqueous or nonaqueous medium, optionally after one of: adjusting the concentration of the cross-linked poly(amino acid) in the dispersion; or after dispersing dry, particulate cross-linked poly(amino acid) in aqueous or nonaqueous medium; or after transfer of the cross-linked poly(amino acid) from a nonaqueous medium to an aqueous medium. The order of the steps can be different in various embodiments, or can be combined; for example, the poly(amino acid) can be polymerized and cross-linked in a single reaction step or the poly(amino acid) can be cross-linked and dried in an single step. In an alternative embodiment, the rheology modifier may be prepared by a method comprising cross-linking, in a nonaqueous medium, a homopolymer of an amino acid that polymerizes to form monomer units that include at least one carboxylic acid side group, a copolymer of at least one amino acid that polymerizes to form monomer units that include one or more carboxylic acid side groups and at least one comonomer, a combination of such homopolymers or copolymers or both, or a polymer blend in which at least one polymer has amino acid monomer units that include one or more carboxylic acid side groups to form a cross-linked poly(amino acid); transferring the cross-linked poly(amino acid) from the nonaqueous medium to an aqueous medium; swelling the cross-linked poly(amino acid) with water; and, if necessary, reducing the cross-linked poly(amino acid) to a particle size that, when fully swollen in deionized water, has a mean equivalent diameter of up to about 1000 µm.

In a third aspect of the invention, methods of using the cross-linked poly(amino acid) rheology modifier to prepare thickened aqueous compositions include steps of: a) dispersing the cross-linked poly(amino acid) into an aqueous medium to form an aqueous dispersion and b) swelling the poly(amino acid) particles with water to thicken the aqueous dispersion. The thickened aqueous dispersion can include other dissolved, emulsified, or dispersed materials, which may be added to the aqueous medium before, during, or after dispersing the cross-linked poly(amino acid) particles. The thickened aqueous dispersion can be combined with other aqueous or nonaqueous compositions.

Mean equivalent spherical diameter of the crosslinked poly(amino acid) particles when fully swollen in deionized water is measured using laser diffraction according to the laser diffraction apparatus and methods described by Prestes, Paula Souza et al., "Particle size and morphological characterization of cosmetic emulsified systems by Optical Coherence Tomography (OCT)," Braz. J. Pharm. Sci. [online], 2016, vol. 52, n. 2, pp. 273-280, where the mean equivalent spherical diameter is represented by D[4,3]— Volume or Mass Moment Mean—De Brouckere Mean Diameter. The crosslinked poly(amino acid) particles are deemed to be fully swollen when there is no further increase in the mean equivalent spherical diameter when measured at 24-hour intervals.

Weight average molecular weight of the uncrosslinked poly(amino acid) polymers is measured by gel permeation chromatography using polyacrylic acid standards, according to the apparatus and methods described by Wang, J., Yuan, H., Wei, X., Chen, J., and Chen, S. (2016), "Enhancement of poly-γ-glutamic acid production by alkaline pH stress treatment in *Bacillus licheniformis* WX-02," J. Chem. Technol. Biotechnol., 91: 2399-2403.

All viscosity measurements are carried out at 25° C.

Additional embodiments are described below.

DETAILED DESCRIPTION

Figure 1:
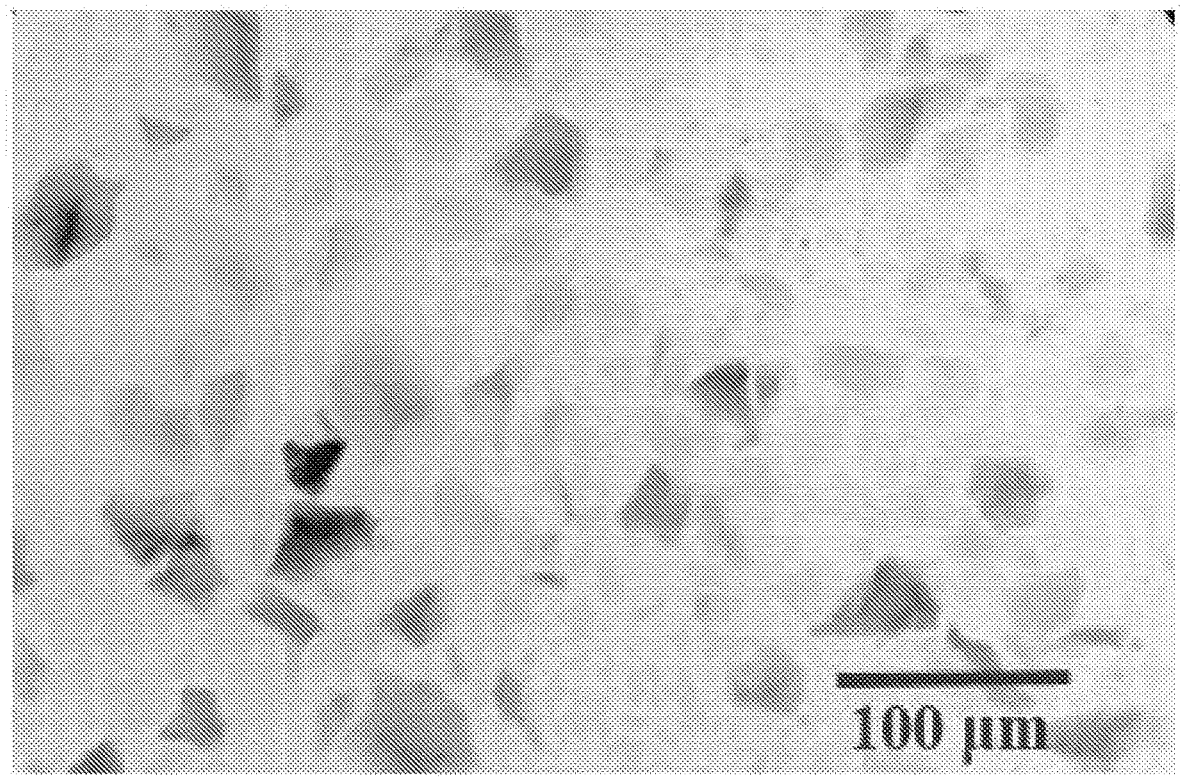
FIG. 1 shows exemplary cross-linked D,L-γ-poly(glutamic acid) microparticles, swollen in deionized water and dyed with methylene blue for contrast, with the photograph taken at a magnification of 200×.

The terms "rheology modifier," "viscosity modifier," "thickening agent," and "thickener" are used interchangeably to refer to polymeric materials that, when added to aqueous compositions, alter the flow properties of the compositions. The term "cross-link" refers to a covalent bond between polymer chains or to the formation of such a covalent cross-link bond between polymer chains. The term "cross-linker" refers to a molecule that can form a cross-link bond between polymer chains. The term "aqueous system" refers to an aqueous medium comprising one or more solutes or dispersed species. The aqueous system may be the aqueous phase of a multi-phase composition such as a water-in-oil emulsion. The term "copolymer" refers to a polymer that comprises two or more different monomer species. Weight by volume percentages (% weight by volume) are calculated as 100 times grams per milliliter (100 times g/mL).

"A," "an," "the," "at least one," and "one or more" are used interchangeably to indicate that at least one of the item is present; a plurality of such items may be present unless the context clearly indicates otherwise. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters. In addition, disclosure of ranges includes disclosure of all values and further divided ranges within the entire range. The terms "comprises," "comprising," "including," and "having," are inclusive and therefore specify the presence of stated features, integers, steps, operations, elements, or components, but do not preclude the presence or addition of one or more other features, integers, steps, operations, elements, components, or groups thereof. As used in this specification, the term "or" includes any and all combinations of one or more of the associated listed items.

The present invention provides a highly effective rheology modifier of particles of cross-linked poly(amino acids) that can be obtained through biobased methods or from renewable starting materials. The cross-linked poly(amino acid) particles can be dispersed in an aqueous system wherein the poly(amino acid) particles swell and thereby thicken the aqueous system.

Surprisingly, the cross-linked poly(amino acid) particles provide superior thickening potency, requiring less thickener to produce a target viscosity or producing a higher viscosity per unit concentration of thickener, as compared to structurally analogous carboxyl-containing polymers based on ethylenically unsaturated monomers. The cross-linked poly (amino acid) particles also surprisingly provide a higher degree of resistance to loss of thickening potency in the presence of electrolytes, especially mono- and polyvalent metal cations, compared to structurally analogous carboxyl-containing polymers based on ethylenically unsaturated monomers.

I. Cross-Linked Poly(Amino Acid) Particle Rheology Modifier Compositions

The rheology modifier composition of this invention includes cross-linked poly(amino acid) particles with a mean equivalent spherical diameter (that is, diameter of a sphere of equivalent volume to the mean volume of the particles) when fully swollen in deionized water of up to about 1000 µm (measured by laser diffraction. The crosslinked-poly (amino acid) particles fully swollen in deionized water may have a mean equivalent spherical diameter of from about 0.1 µm or from about 0.5 µm or from about 1 µm up to about 1000 µm or up to about 500 µm or up to about 100 µm or up to about 75 µm or up to about 50 µm or up to about 25 µm. Among the included ranges that may be mentioned for the mean equivalent spherical diameter of the cross-linked poly (amino acid) particles when fully swollen in deionized water are from about 0.1 µm up to about 1000 µm; from about 0.1 µm up to about 500 µm; from about 1 µm up to about 500 µm; from about 1 µm up to about 100 µm; from about 1 µm up to about 75 µm; from about 1 µm up to about 50 µm; and from about 1 µm up to about 25 µm.

The thickening potency and uniformity of the rheology modifier composition may be maximized when the amino acid monomer composition of the poly(amino acid) and cross-linking bonds thereof are selected to render insoluble hydrogel materials, which have a hydrophilic structure capable of swelling and holding large amounts of water in the resulting swollen three-dimensional networks of cross-linked poly(amino acid) in the particles. The properties of the rheology modifier composition can be optimized for a particular application or use via selection of different cross-linkers, by modulating the composition and weight average molecular weight of the linear poly(amino acid), or by altering the ratio of cross-link bonds to amino acid monomer units. While not wishing to be bound by theory, it is believed that the thickening potency of cross-linked poly(amino acid) is markedly influenced by the ratio of cross-link bonds to amino acid monomer units, which in turn controls the degree of swelling of the hydrogel. Dispersions of highly cross-linked poly(amino acid) particles generally can be expected to have a low viscosity and grainy texture, corresponding to a low degree of swelling and high elastic modulus of the poly(amino acid) hydrogel material, whereas dispersions of lightly cross-linked poly(amino acid) particles generally can be expected to yield thick gels with a smooth texture, corresponding to a high degree of swelling and low elastic modulus of the poly(amino acid) hydrogel material. Thickening potency may also increase with increasing weight average molecular weight, such as when the weight average molecular weight is at least about one million Daltons. For most practical applications, the poly(amino acid) hydrogels may have a free-swelling absorbency in the range of from about 20 g deionized water per g dry poly(amino acid) hydrogel to about 10,000 g water per g dry poly(amino acid) hydrogel to provide a suitable rheology modifier; preferred ranges include 50 g deionized water per g dry poly(amino acid) hydrogel to about 2,000 g water per g dry poly(amino acid) hydrogel and 50 g deionized water per g dry poly (amino acid) hydrogel to about 1,000 g water per g dry poly(amino acid) hydrogel.

In addition to the chemical composition of the cross-linked poly(amino acid), rheology properties are strongly influenced by particle size. Large particles (mean equivalent spherical diameter >500 µm) yield distinctly grainy dispersions, while smaller particles (mean equivalent spherical diameter <150 µm) yield thicker, more homogenous dispersions. Particle size can be controlled, for example, by mechanically grinding the cross-linked poly(amino acid) in powder form or as a slurry or dispersion using, for example, jet mills, attritors, or micro-mills.

Finally, the cross-linked poly(amino acid) particles can be prepared in acidic form (wherein the amino acid carboxylic acid side groups are fully protonated) or in salt form, neutralized with a cationic species (wherein the amino acid carboxylic acid side groups are deprotonated and in anionic form). Examples of suitable cationic species include, but are not limited to, $K^+$, $Na^+$, $NH_4^+$, $Ca^{2+}$, and $Mg^{3+}$. In acidic form, the cross-linked poly(amino acid) particles will generally have a low degree of swelling, but can be readily dispersed in water.

A) Poly(amino acids)

The cross-linked poly(amino acids) of the invention comprise covalently cross-linked linear homopolymers or copolymers comprising amino acid monomer units having one or more carboxylic acid side groups. In the copolymers, the amino acid monomer units having carboxylic acid side group should be at least about 60% by weight of the poly(amino acid) copolymer, preferably from about 60% to 100% by weight and more preferably from about 90% to about 100% by weight of the poly(amino acid) copolymer. In the case of a crosslinked blend of different poly(amino acids), each poly(amino acid) preferably has amino acid monomer units having carboxylic acid side groups and the amino acid monomer units having carboxylic acid side groups preferably should be at least about 60% by weight of each polymer of the blend, preferably from about 60% to 100% by weight and more preferably from about 90% to about 100% by weight of each poly(amino acid) copolymer in the blend. While not wishing to be bound by theory, it is believed that a higher percentage by weight of monomer units with carboxylic acid side groups increases the hydrophilic nature of the cross-linked poly(amino acid) materials, leading to desired swelling behavior and resulting in hydrogel materials with favorable thickening properties. Examples of amino acid monomer units with one or more carboxylic acid side groups include, but are not limited to, aspartic acid, glutamic acid, and γ-carboxyglutamate monomer units. Nonlimiting examples of suitable comonomers include alanine, cysteine, phenylalanine, glycine, histidine, isoleucine, lysine, leucine, methionine, asparagine, pyrrolysine, proline, glutamine, arginine, serine, threonine, selenocysteine, valine, tryptophan, tyrosine, carnitine, γ-aminobutyric acid, levothyroxine, hydroxyproline, selenomethionine and combinations of these. The poly(amino acids) may be polymerized by typical condensation polymerization techniques for polyamides or, preferably, by biosynthesis, such as through a ribosomal translation method or through non-ribosomal synthesis in a microbial fermentation or in vitro biochemical method, which produces only linear polymers.

The cross-linked poly(amino acids) may have a weight average molecular weight of from about 1000 Da or from about 5000 Da or from about 10,000 Da or from about 20,000 Da or from about 30,000 Da or from about 50,000 Da or from about 100,000 Da or from about 150,000 Da or from about 200,000 Da or from about 250,000 Da or from about 300,000 Da or from about 400,000 Da or from about 500,000 Da or from about 1,000,000 Da or from about 2,000,000 Da or from about 5,000,000 Da up to about 10,000,000 Da or up to about 15,000,000 Da or up to about 20,000,000 Da or up to about 25,000,000 Da or up to about 30,000,000 Da. Among the specific included ranges that may be mentioned for the weight average molecular of the poly(amino acid) are from about 1000 Da up to about 30,000,000 Da or from about 100,000 Da up to about 15,000,000 Da or from about 500,000 Da up to about 15,000,000 Da or from about 1,000,000 Da up to about 15,000,000 Da or from about 2,000,000 Da up to about 15,000,000 Da or from about 3,000,000 Da up to about 10,000,000 Da or from about 5,000,000 Da up to about 10,000,000 Da.

The linear amino acid polymers are cross-linked to one another through a covalent bond between carboxylic acid side groups, at a ratio ranging from 1 cross-link bond per 10 amino acid monomer units to 1 cross-link bond per about 100,000 amino acid monomer units. In various embodiments, the cross-link ratio may be from 1 cross-link bond per 10 or per about 50 or per about 100 amino acid monomer units up to 1 cross-link bond per about 500 or per about 1000 or per about 10,000 or per about 50,000 or per about 100,000 amino acid monomer units. Particular including ranges that may be mentioned are cross-link ratios of from 1 cross-link bond per 10 amino acid monomer units to 1 cross-link bond per about 10,000 amino acid monomer units or from 1 cross-link bond per 50 amino acid monomer units to 1 cross-link bond per about 10,000 amino acid monomer units or from 1 cross-link bond per 100 amino acid monomer units to 1 cross-link bond per about 10,000 amino acid monomer units or from 1 cross-link bond per 100 amino acid monomer units to 1 cross-link bond per about 5,000 amino acid monomer units or from 1 cross-link bond per 500 amino acid monomer units to 1 cross-link bond per about 5,000 amino acid monomer units or from 1 cross-link bond per 500 amino acid monomer units to 1 cross-link bond per about 1,000 amino acid monomer units. Blends of different linear polymers of amino acids of various compositions (including amino acids that provide the required carboxylic acid side groups) and molecular weights may be utilized. In some embodiments, the amino acid monomer units are of biological origin and produced from a renewable feedstock. The linear polymers of amino acids can be prepared or obtained commercially.

In some embodiments, the cross-linked poly(amino acid) is prepared using a homopolymer of aspartic or glutamic acid. In some embodiments, the cross-linked poly(amino acid) is prepared using L-α-poly(aspartate) or L-α-poly (glutamate) or combinations thereof produced through a ribosomal translation method. In some embodiments, the cross-linked poly(amino acid) is prepared using D,L-(α,β)-poly(aspartate) or D,L-(α, γ)-poly(glutamate) or combinations thereof, produced from aspartic acid and/or glutamic acid monomers through condensation polymerization. In some embodiments, the cross-linked poly(amino acid) is prepared using D-γ-poly(glutamate), L-γ-poly(glutamate), D,L-γ-poly(glutamate) or any combination of these produced through non-ribosomal synthesis in a microbial fermentation or in vitro biochemical method.

B) Cross-Linkers

In some embodiments, the cross-link bonds are formed between carboxylic acid side groups on the linear amino acid polymer molecules. Examples of cross-link bonds between carboxylic acid side groups include, but are not limited to, cross-link bonds formed via actinic irradiation such as gamma or electron beam radiation, cross-link bonds formed via reaction of carboxylic acid side groups with a cross-linking molecule containing two or more groups reactive with carboxyl groups such as epoxide or aziridine groups, cross-link bonds formed via reaction of carboxylic acid side groups with a carbodiimide compound to form an O-acylisourea intermediate that subsequently reacts with a cross-linking molecule containing two or more reactive amine groups, and cross-link bonds formed via reaction of carboxylic acid side groups with a compound containing a glycidyl group and an ethylenically unsaturated group, with subsequent cross-linking via free radical or addition polymerization of the added ethylenically unsaturated group. In some embodiments, the cross-linker is produced from a renewable feedstock. The present invention is not limited to any particular type of cross-link bond between the poly (amino acid) polymers, a variety of which, including all those disclosed herein, can be prepared by methods known to persons skilled in the art.

Examples of suitable cross-linking molecules containing two or more reactive epoxide groups include, but are not limited to, polyglycidyl ethers of alkanepolyols and poly (alkylene glycols), including, for further example, ethylene glycol diglycidyl ether, diethylene glycol diglycidyl ether, polyethylene glycol diglycidyl ether, glycerine diglycidyl ether and triglycidyl ether, propylene glycol diglycidyl ether and butanediol diglycidyl ether. Additional suitable cross-linkers of this type include, for example, polyglycidyl ethers of erythritol, trimethylolethane, pentaerythritol, and trimethyolpropane. Further examples include diepoxyalkanes and diepoxyaralkanes, including, for further example, 1,2, 3,4-diepoxybutane, 1,2,4,5-diepoxypentane, 1,2,5,6-diepoxyhexane, 1,2,7,8-diepoxyoctane, 1,4- and 1,3-divinylbenzene diepoxides; polyphenol polyglycidyl ethers, including, for further example, 4,4'-isopropylidenediphenol diglycidyl ether (bisphenol A diglycidyl ether) and hydroquinone diglycidyl ether. In some embodiments, polyglycidyl ethers of alkanepolyols and poly(alkylene glycols) cross-linkers are selected, on the basis of forming biodegradable cross-link bonds and having degradation products of low toxicity.

Examples of suitable cross-linking molecules containing two or more reactive aziridine groups include, but are not limited to, polyaziridinyl derivatives of alkanepolyols, including for further example, pentaerythritol-tris-3-(N-aziridinyl)propionate, trimethylolpropane-tris-3-(N-aziridinyl)propionate, pentaerythritol-bis-3-(N-aziridinyl)propionate, and trimethylolpropane-bis-3-(N-aziridinyl) propionate. Further examples include polyaziridinyl derivatives of propionate esters of erythritol, pentaerythritol, trimethylolethane, and trimethyolpropane, which may be prepared by addition of aziridine to the corresponding acrylate esters of the polyols.

In various embodiments, the cross-linker has three or more functional groups reactive with the carboxyl groups of the poly(amino acid). In certain embodiments, it may be preferred to use a triglycidyl ether, tetraglycidyl ether, or tri- or tetraaziridinyl derivative of an alkanepolyol, such as one of the examples already mentioned.

In various embodiments, the poly(amino acid) may be crosslinked by heating a solution of the poly(amino acid) and a cross-linker in water at a temperature at which the water evaporates and the cross-linker reacts with the poly (amino acid).

C) Particles

Cross-linked poly(amino acid) micro particles can be produced using methods such as, but not limited to, mechanical grinding or homogenization methods, including for further example, micronization of a dried cross-linked poly(amino acid) material or homogenization of a hydrated cross-linked poly(amino acid) material. The mechanical grinding or homogenization apparatus can be suitably selected and configured to reduce cross-linked poly(amino acid) materials to particles with a mean equivalent spherical diameter (that is, diameter of a sphere of equivalent volume to the mean volume of the particles) of less than 1000 when fully swollen in deionized water. The present disclosure is not limited to any particular particle shape or geometry. Examples of particle geometries include, but are not limited to, irregular granular particles, spheres, ellipsoids, and cylindrically-shaped particles (or whiskers).

D) Other Variations and Embodiments

In some embodiments, the composition of particles of cross-linked poly(amino acids) further comprises excipients or additives added to enhance performance or ease of use in end applications. The present disclosure is not limited to any particular type of excipient or additive. Examples include, but are not limited to, other molecular species that are cross-linked with the poly(amino acids) to alter material properties, surfactants or emulsifiers to enhance dispersion, coating the particles of cross-linked poly(amino acids) with an active formulation ingredient, or impregnating the particles of cross-linked poly(amino acids) with an active formulation ingredient.

II. Methods of Using the Cross-Linked Poly(Amino Acid) Compositions as Rheology Modifiers in Aqueous Systems and Formulations The cross-linked poly(amino acid) particle compositions are beneficial for thickening aqueous systems in a wide variety of applications and contexts and can be used in a manner similar to conventional thickeners. Examples of aqueous systems that may be prepared by the methods of the invention include, but are not limited to, personal care and pharmaceutical formulations (which may include topical drug formulations, skin care products, cosmetics, and cleansing products), paints, coatings, and inks, agrochemical formulations, food products, concrete and cement mixes, household and industrial cleaners, and drilling fluids. The utility of biodegradable and non-toxic embodiments of cross-linked poly(amino acid) particle compositions is readily apparent for applications that involve ingestion (such as food and medications), direct or indirect skin contact (such as personal care and pharmaceutical formulations), or environmental release (such as agrochemical formulations and drilling fluids). Furthermore, the superior thickening potency (that is, the minimum amount of thickener to produce a target viscosity or the viscosity produced per unit concentration of thickener) and a higher degree of resistance to electrolytes (that is, to loss of thickening potency), especially mono- and polyvalent metal cations, compared to structurally analogous synthetic carboxyl-containing polymer rheology modifiers based on ethylenically unsaturated monomers, offers performance benefits in applications where cost and the presence of high electrolyte concentrations may be of concern, such as concrete and cement mixes and drilling fluids.

The methods of using the cross-linked poly(amino acid) particle compositions as rheology modifiers in aqueous systems comprise: a) dispersing the composition into an aqueous system, such as at a concentration of 1 g/L to 100 g/L, under mixing to form a dispersion, and b) mixing the dispersion formed in step a) to swell the poly(amino acid) particles and thicken the aqueous system. In some embodiments, the poly(amino acid) particle composition used in step a) is at an acidic pH, such that the carboxylic acid side groups are partially or fully protonated, which aids in dispersion. Examples of suitable pH values are pH values of about 4 to about 7 or of about 5 to about 7 or of about 5.5 to about 7. The pH may also be basic with the caveat that a basic pH is not detrimental to stability.

In some embodiments, the poly(amino acid) particle composition used in step a) is partially hydrated or dispersed in an aqueous composition, at a concentration ranging from 0.1 g/L to 1000 g/L, or from 1 g/L to 1000 g/L, or from 1 g/L to 100 g/L, or from 1 g/L to 30 g/L, or from 1 g/L to 10 g/L before addition to the aqueous system to be thickened. In some embodiments, the poly(amino acid) particle composition used in step a) is dispersed in a hydrophobic phase of any composition at a concentration ranging from 0.1 g/L to 1000 g/L, or from 1 g/L to 1000 g/L, or from 1 g/L to 100 g/L, or from 1 g/L to 30 g/L, or from 1 g/L to 10 g/L before being dispersed into the aqueous phase, thereby aiding dispersion. In some embodiments, the cross-linked poly (amino acid) particle composition used in step a) is a dried powder, which in other applications may be considered a less advantageous variation due to the difficulties in re-swelling dry powder and electrostatic charge effects which make the powder difficult to handle, but nonetheless is feasible. In some embodiments, step b) further comprises adjusting the pH of the aqueous dispersion through addition of any alkali or acidic agent, such as from pH of about 4 to a pH of about 5 or about 5.5 or about 6 or about 7 or to a basic pH such as 7.5 or 8 (provided a basic pH is not detrimental to stability), or from pH of about 5 to a pH of about 5.5 or about 6 or about 7 or to a basic pH such as 7.5 or 8 (provided a basic pH is not detrimental to stability), thereby changing the degree of swelling. Such an approach can be useful when the cross-linked poly(amino acid) composition is added in acidic form, as the cross-linked poly (amino acid) composition can be easily dispersed in unswollen acidic form and then adjusted to a final pH that achieves a desired swelling and thickening. In some embodiments, step a) further comprises adjusting the pH of the aqueous system through addition of any alkali or acidic agent prior to dispersion of the said poly(amino acid) composition, such that the final pH of the dispersion permits the desired thickening. This approach is useful when the cross-linked poly(amino acid) composition is added in acidic form, permitting nearly instantaneous thickening.

EXAMPLES

The following examples are provided in order to demonstrate and further illustrate certain preferred embodiments and aspects of the present invention and are not to be construed as limiting the scope thereof.

Example 1

Figure 2:
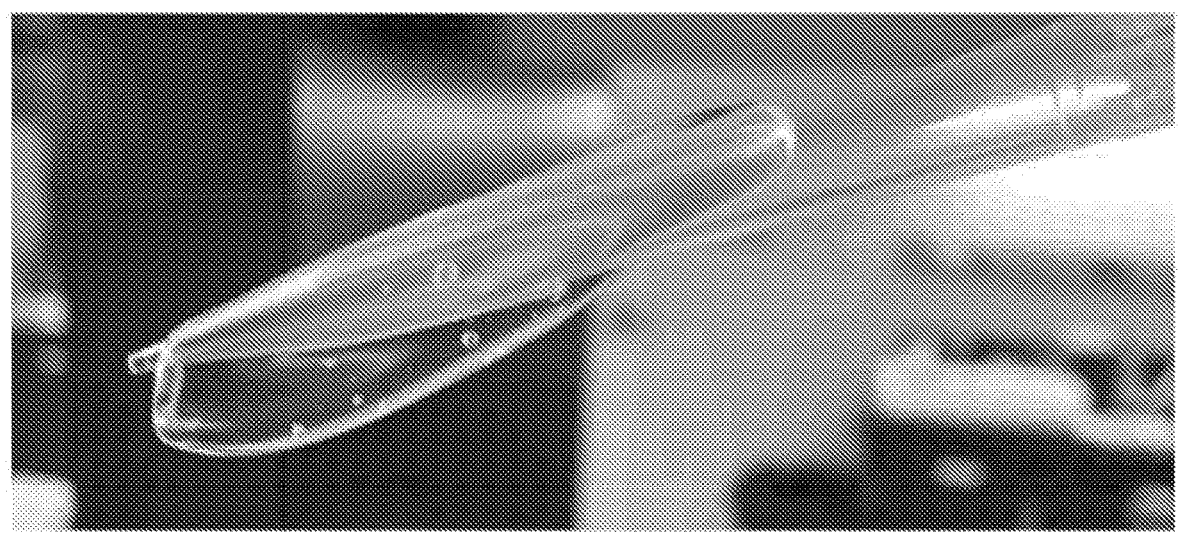
FIG. 2 shows an exemplary aqueous composition thickened via dispersion and swelling of cross-linked D,L-γ-poly(glutamic acid) microparticles, at concentration of 1.3% weight by volume, with the photograph taken at a magnification of 1×.

Preparation of Cross-Linked Poly(amino acid) Microparticles 4.61 g of linear sodium D,L-γ-poly(glutamate), with a weight average molecular weight of 700,000 Daltons (obtained from Lubon Chemical Company, Jiangsu, China) was dissolved in 46.1 mL deionized water and 46.1 µL 4M HCl was added to adjust the pH of the solution to 5.8, then 46.1 µL of the cross-linker ethylene glycol diglycidyl ether was mixed into the solution. The resulting mixture was poured into a PYREX® glass tray and baked at 150° C. for 60 minutes to cross-link the D,L-γ-poly(glutamate) with the ethylene glycol diglycidyl ether. The dried, crosslinked resin formed from the baking process was removed from the oven and allowed to cool to room temperature (~25° C.) for 15 minutes. Approximately 1 L of deionized water was added, causing the cross-linked resin to immediately rehydrate and swell. The rehydrated material was placed in a mesh bag and soaked in 2 gallons of deionized water for three days, with the water changed daily, to remove residual uncross-linked material. The hydrated material was then dried at 40° C. for 24 hours, yielding 3.2 g of purified cross-linked D,L-γ-poly (glutamate). 1.33 g of the purified cross-linked D,L-γ-poly (glutamate) was ground to a fine powder (100 mesh), dispersed in 100 mL deionized water, and homogenized for 20 minutes with a Miallegro 9090 Mitutto 550-Watt Immersion Blender to yield a dispersion of cross-linked D,L-γ-poly(glutamate) micro particles with a concentration of 1.33% weight by volume. A 5 µL aliquot of the dispersion was combined with 5 µL of 1 mg/mL methylene blue solution to stain the particles for visualization purposes and examined under 200× magnification with a brightfield microscope, revealing irregularly shaped cross-linked D,L-γ-poly(glutamate) micro particles with an approximate mean diameter of 50 µm, shown in FIG. 1. For comparative purposes, a photograph at 1× magnification of the cross-linked D,L-γ-poly(glutamate) micro particle dispersion is shown in FIG. 2.

Example 2 (Comparative)

Preparation of Cross-Linked Polyacrylate Microparticles as Structurally Analogous Prior Art Composition for Comparison to Example 1

4.61 g of linear polyacrylic acid with a weight average molecular weight of 240,000 Daltons (obtained from Sigma Chemical) was dissolved in 46.1 mL deionized water. 1.38 mL of 4M NaOH was added to adjust the pH of the solution to 5.8. The solution was then cross-linked and used to prepare a micro particle dispersion, identically to the procedure of Example 1.

Example 3

Viscosity Measurements of the Microparticle Dispersions Produced in Examples 1 and 2

Figure 3:
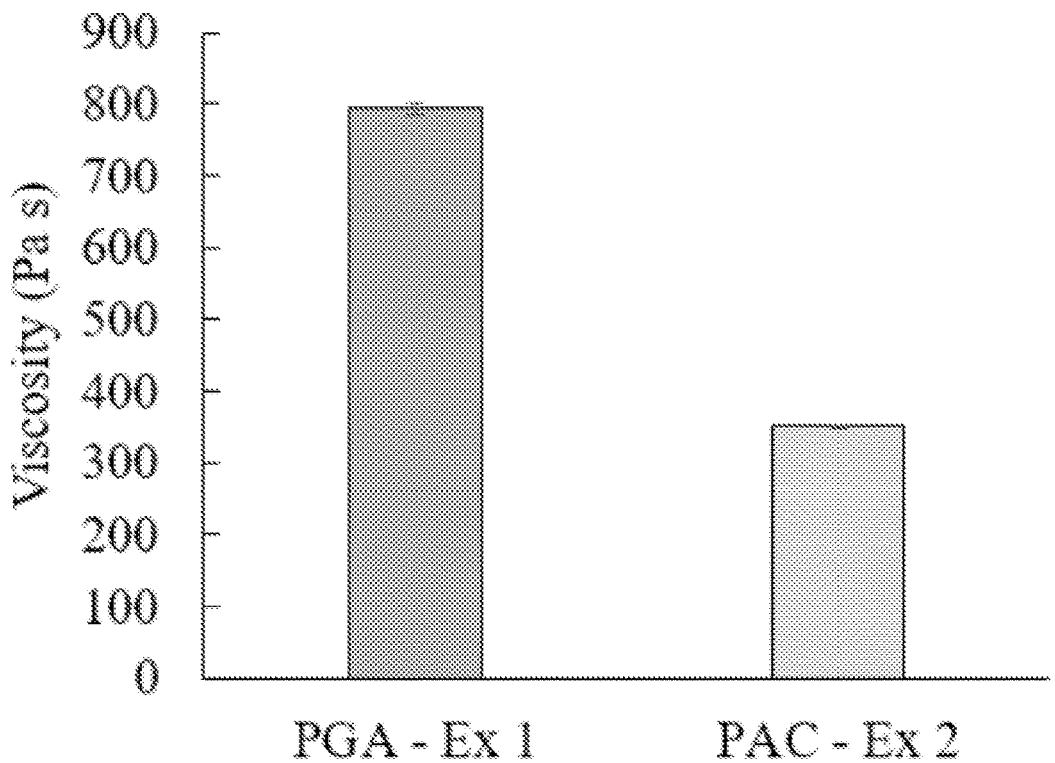
FIG. 3 shows the viscosity (Pa s) of an aqueous dispersion (containing deionized water) of cross-linked D,L-γ-poly(glutamic acid) microparticles ("PGA—Ex 1") at 1.3% weight by volume compared to an aqueous dispersion (containing deionized water) cross-linked polyacrylate microparticles ("PAC—Ex 2") prepared as an analogous composition, at 1.3% weight by volume.

For comparative purposes, the viscosities of the microparticle dispersions prepared in Examples 1 and 2 were measured at 25° C. via falling sphere method. 80 mL aliquots of each dispersion were transferred to 100 mL graduated cylinders, giving a liquid height of 0.0145 m. For each dispersion, replicate measurements were made of the transit time required for a small steel sphere (d=0.0045 m; p=8050 kg/m3) to fall through the depth of the dispersion. Estimated viscosity values were calculated as per Stokes' law, shown in FIG. 3. While this viscosity measurement method is better suited for Newtonian fluids, these data serve to illustrate that cross-linked D,L-γ-poly(glutamate) microparticle dispersions are perceptibly thicker than the prior art, structurally analogous, cross-linked polyacrylate microparticle dispersions (with similar particle sizes, identical cross-linkers, similar cross-linking ratios, and identical dispersion concentrations).

Figure 4:
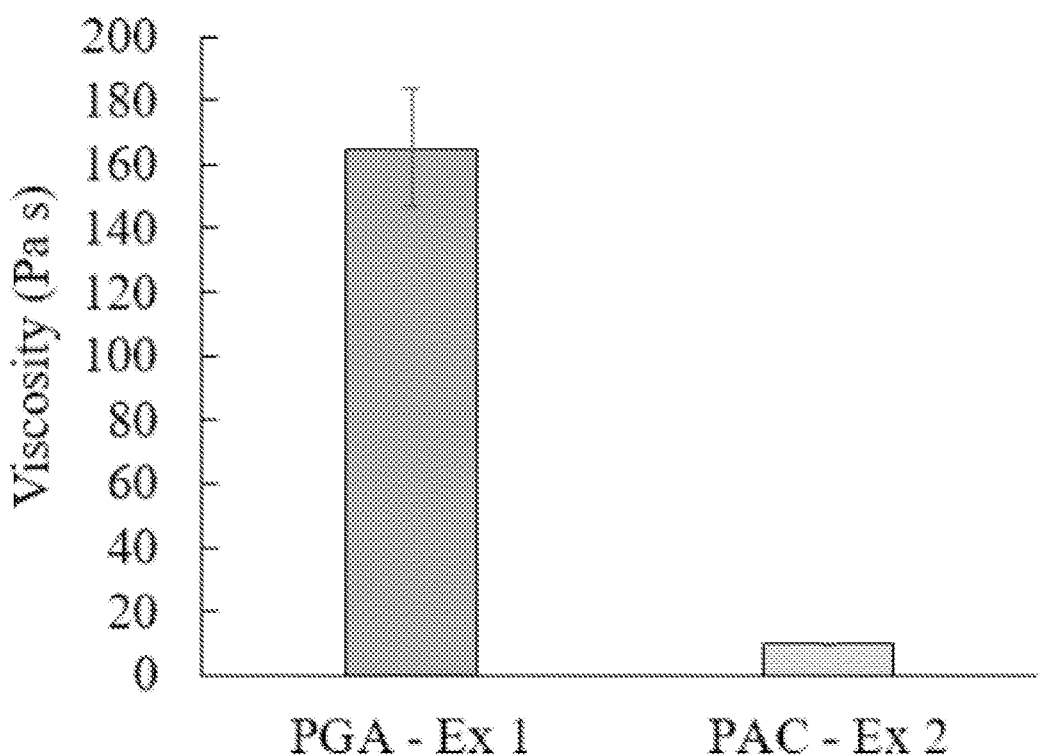
FIG. 4 shows the viscosity (Pa s) of an aqueous dispersion (containing 5.8 mg/L of NaCl, 13.7 mg/L KCl, 2.9 mg/L of $NH_4Cl$, 27.5 mg/L of $MgCl_2$, 85.7 mg/L of $CaCl_2$, and 0.16 mg/L of $FeCl_3$) of cross-linked polyglutamic acid microparticles ("PGA—Ex 1") at 1.22% weight by volume compared to an aqueous dispersion (containing 5.8 mg/L of NaCl, 13.7 mg/L KCl, 2.9 mg/L of $NH_4Cl$, 27.5 mg/L of $MgCl_2$, 85.7 mg/L of $CaCl_2$, and 0.16 mg/L of $FeCl_3$) of cross-linked polyacrylate microparticles ("PAC—Ex 2") prepared as an analogous composition, at 1.22% weight by volume.
Figure 5:
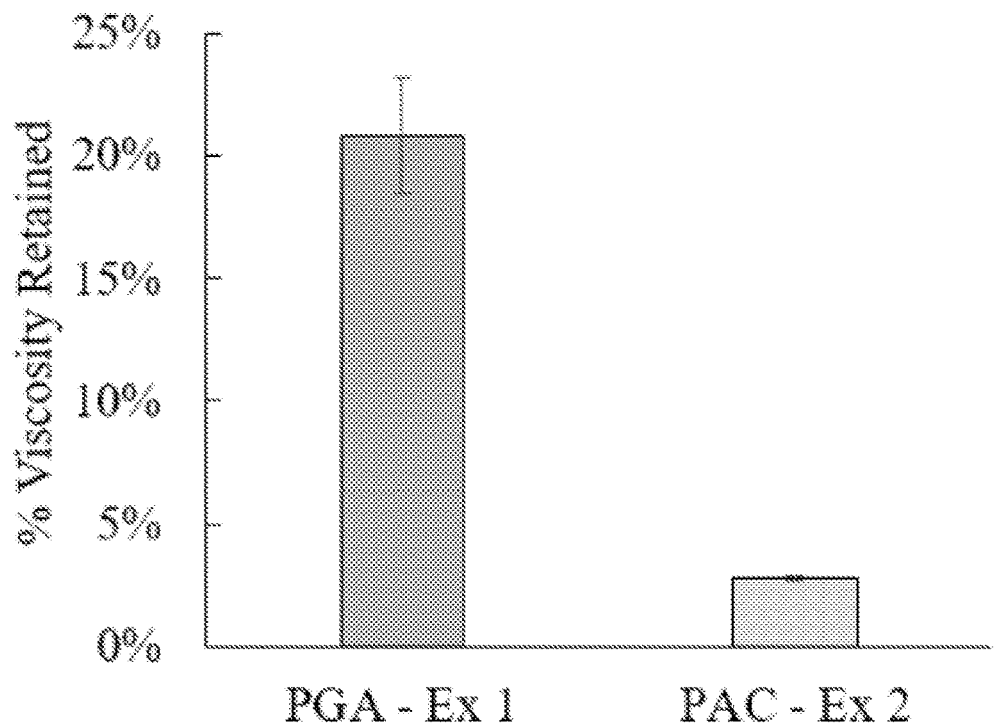
FIG. 5 shows the percentage of original viscosity shown in FIG. 3 after the treatment described for FIG. 4.

To test the resistance of each dispersion to electrolytes, particularly divalent metal cations, an electrolyte solution was added to 90 mL aliquots of each of the dispersions prepared in Examples 1 and 2 to yield final electrolyte concentrations of 5.8 mg/L of NaCl, 13.7 mg/L KCl, 2.9 mg/L of $NH_4Cl$, 27.5 mg/L of $MgCl_2$, 85.7 mg/L of $CaCl_2$, and 0.16 mg/L of $FeCl_3$. The viscosity measurement test described above was repeated, with the data shown in FIG. 4. The percentage of viscosity retained in the treated (that is, electrolyte solution added) vs. untreated (that is, the baseline viscosity measurement in deionized water) dispersions is shown in FIG. 5. These data clearly show that cross-linked D,L-γ-poly(glutamate) microparticle dispersions have seven-fold higher electrolyte resistance in terms of retained viscosity compared to the structurally analogous cross-linked polyacrylic acid microparticle dispersions (with similar particle sizes, identical cross-linkers, similar cross-linking ratios, and identical dispersion concentrations).

Example 4

Method of Preparing Acid-Precipitated Cross-Linked Poly (Amino Acid) Microparticle Concentrate and its Use to Thicken Aqueous System 600 mL of a cross-linked D,L-γ-poly(glutamate) microparticle dispersion prepared similarly to that described in Example 1, but with a dispersed particle concentration of 0.89% weight by volume. 3.2 mL of 4 M HCl was added to the dispersion to reduce the pH to 3, causing the microparticles to de-swell and precipitate from the dispersion. The acidified dispersion was centrifuged at 1,500×g for 30 minutes to collect the acid-precipitated cross-linked D,L-γ-poly(glutamate) microparticles. A pellet of precipitated cross-linked D,L-γ-poly(glutamate) microparticles was collected, and a small aliquot was taken for gravimetric analysis (drying overnight at 90° C.) to measure the concentration (dry weight basis) of the precipitated microparticle slurry, which was determined to be 5.84% weight by volume.

The acid-precipitated microparticle concentrate was then used to thicken deionized water. 150 mL of deionized water was placed in a beaker and mixed with a Miallegro 9090 Mitutto 550-Watt Immersion Blender on the lowest speed setting. 25.7 g of the acid-precipitated microparticle concentrate was added, resulting in no perceptible increase in viscosity. Then, 1.75 mL of 4 M NaOH was added to neutralize and re-swell the acid-precipitated microparticle dispersion. The dispersion was rapidly (within 10 seconds) and evenly thickened upon addition of the 4 M NaOH aliquot, illustrating the general ease and utility of the thickening method.

Example 5

Figure 6:
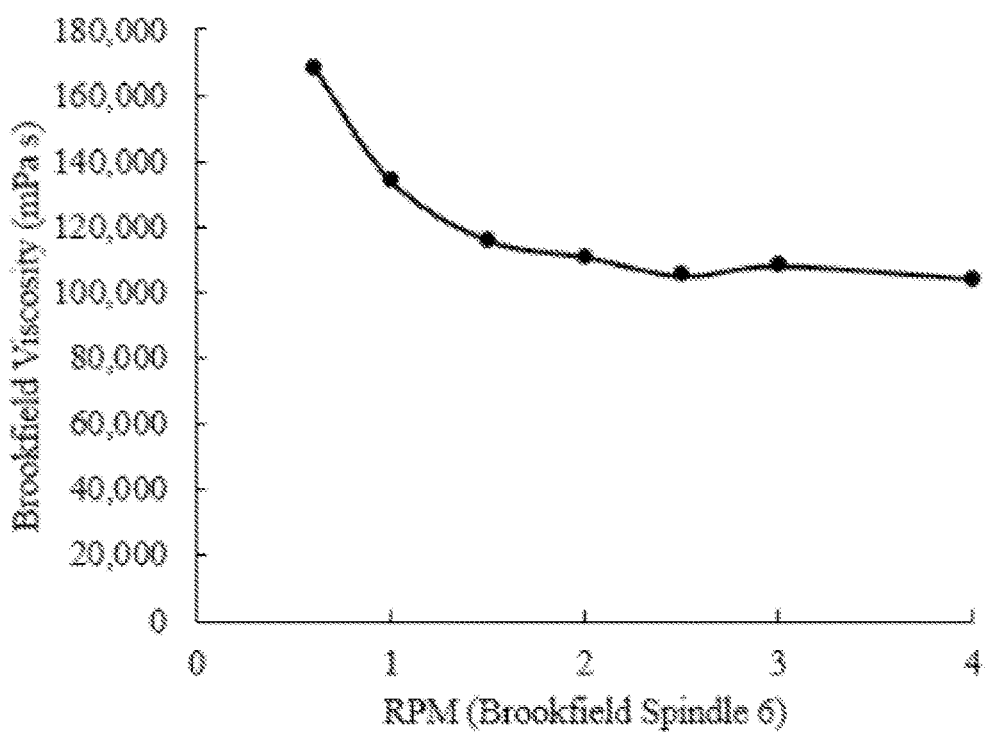
FIG. 6 shows Brookfield viscosity measurements at 25° C., using Brookfield spindle 6 over a range of rotational speeds from 0.6 to 4 RPM, for a 1% weight by volume dispersion of D,L-γ-poly(glutamic acid) microparticles in deionized water.
Figure 7:
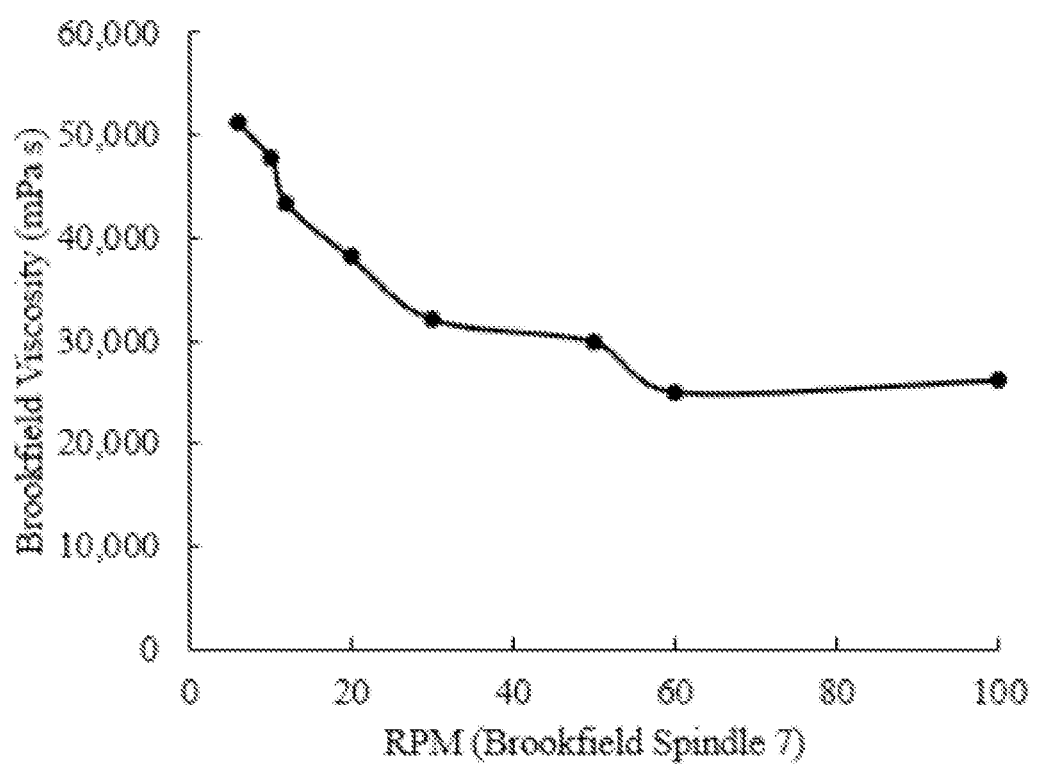
FIG. 7 shows Brookfield viscosity measurements at 25° C., using Brookfield spindle 7 over a range of rotational speeds from 6 to 100 RPM, for a 1% weight by volume dispersion of D,L-γ-poly(glutamic acid) microparticles in deionized water.

Preparation of Cross-Linked Poly(amino acid) Microparticles and Measurement of Brookfield Viscosity Values of 1% Weight by Volume Dispersion 600 mL of a cross-linked D,L-γ-poly(glutamate) microparticle dispersion was prepared similarly to that described in Example 1, but with a dispersed particle concentration of 1% weight by volume. Brookfield viscosity at 25° C. (in units of millipascal-second; mPa s) of the dispersion at various shear rates (that is, spindle rotational speeds) was determined using a Brookfield AMETEK Medium-Range Viscometer, as per the manufacturer's provided instructions. Brookfield viscosity measurements using Brookfield RV Spindle 6, over a range of rotational speeds from 0.6 to 4 RPM, are shown in FIG. 6. FIG. 7 shows measurements using Brookfield RV Spindle 7 over a range of rotational speeds from 6 to 100 RPM. These results demonstrate that the microparticle dispersion is a shear-thinning fluid and delivers a viscosity profile favorable for use in topical personal care formulations.

Example 6

Preparation and Comparison of Cross-Linked Poly(Amino Acid) Microparticles with Tri-Functional Cross-Linker 2 g of linear sodium D,L-γ-poly(glutamate), with a weight average molecular weight of 700,000 Daltons (obtained from Lubon Chemical Company, Jiangsu, China) was dissolved in 20 mL deionized water. 20 μL 4M HCl was added to adjust the pH of the solution to 5.8, and 23.6 μL of the cross-linker trimethylolpropane triglycidyl ether was then mixed into the solution. The resulting mixture was poured into a PYREX® glass tray and baked at 150° C. for 60 minutes to cross-link the D,L-γ-poly(glutamate) with the trimethylolpropane triglycidyl ether. The dried resin formed from the baking process was removed from the oven and allowed to cool to room temperature (~25° C.) for 15 minutes. Approximately 0.5 L of deionized water was added to the dried material, causing the cross-linked resin to immediately rehydrate and swell. The rehydrated material was placed in a mesh bag and soaked in 1 gallon of deionized water for three days, with the water changed daily, to remove residual uncross-linked material. The hydrated material was then dried at 40° C. for 24 hours, yielding 1.4 g of purified cross-linked D,L-γ-poly(glutamate). The 1.4 g of dried cross-linked D,L-γ-poly(glutamate) was ground to a fine powder (100 mesh), dispersed in 280 mL deionized water, and homogenized for 20 minutes with a Miallegro 9090 Mitutto 550-Watt Immersion Blender to yield a dispersion of cross-linked D,L-γ-poly(glutamate) micro particles with a concentration of 0.5% weight by volume. A comparative sample of D,L-γ-poly(glutamate) cross-linked with ethylene glycol diglycidyl ether was prepared similarly to Example 1, but with a dispersed particle concentration of 0.5% weight by volume. Brookfield viscosity (in units of millipascal-second; mPa s) was determined using a Brookfield AMETEK Medium-Range Viscometer, as per the manufacturer's provided instructions. The Brookfield viscosity of the 0.5% dispersion of D,L-γ-poly(glutamate) micro particles cross-linked with ethylene glycol diglycidyl ether was measured as 142±8 mPa s (100 RPM, RV Spindle 3), while the Brookfield viscosity of the 0.5% dispersion of D,L-γ-poly(glutamate) micro particles cross-linked with trimethylolpropane triglycidyl ether was measured as 5,500±400 mPa s (10 RPM, RV Spindle 3; measurements >10 RPM exceed the torque limits for RV Spindle 3, due to high viscosity). These results demonstrate that superior thickening was achieved through using trimethylolpropane triglycidyl ether, a tri-functional cross-linker, compared to glycol diglycidyl ether, a difunctional cross-linker.

Example 7

Preparation of a Cosmetic Composition Thickened with Cross-Linked Poly(Amino Acid) Microparticles A panel of lotion formulations, thickened with microparticles of D,L-γ-poly(glutamate) cross-linked with the ethylene glycol diglycidyl ether (prepared similarly to Example 1) at dispersions of 0.25% w/v, 0.5% w/v, and 1% w/v, was prepared as per the following procedure:
1. Aqueous phase
   a. Add 1020 g water to a beaker on a hot plate at 75 C, stirring continuously
   b. Add 36 g glycerin
   c. Add 2.46 g sodium EDTA
   d. Allow mixture to settle at 75° C.
   e. Divide the aliquot equally between 3 beakers
   f. Add 1, 2, and 4 grams of D,L-γ-poly(glutamate) cross-linked with the ethylene glycol diglycidyl ether to each respective beaker
   g. Maintain each beaker at 75° C. for at least 20 minutes
2. Oil phase:
   a. Add 18 g Jojoba Oil and 18 g Rice Bran Oil to a beaker, stirring continuously
   b. Add 24 g cetyl alcohol
   c. Add 12 g sorbitan stearate
   d. Add 12 g polysorbate 60
   e. Add 24 g cetereth-20
   f. Bring mixture to 75° C.
   g. Divide aliquot into 3 equal parts
3. Without allowing either mixture time to cool, begin mixing one aliquot of the aqueous phase with immersion blender
4. Gradually add one aliquot of the oil phase
5. Continue mixing for 5 minutes
6. Allow emulsion to cool to 45° C. while periodically pulsing with immersion blender 7. After emulsion has reached 45° C., mix together separately and add the cool-down phase:
    a. 1.6 g Lavender aerosol
    b. 0.4 g Germall plus
    c. Additional water (20 g) to account for evaporation
8. Repeat with 2 remaining aliquots of aqueous and oil phases
9. De-gas 1 minute
10. Adjust pH to 7

The Brookfield viscosities of the lotion formulations were measured similarly to Example 5, using Brookfield RV Spindle 2:

| RPM | .25% PGA mPa s | .5% PGA mPa s | 1.0% PGA mPa s |
|---|---|---|---|
| 100 | 94* | 383 | Over |
| 60 | 76.7* | 404 | Over |
| 50 | 75.2* | 456 | Over |
| 30 | 74.7* | 504 | 1100 |
| 20 | 78* | 576.0 | 1244 |
| 12 | 83.33* | 746.7 | 1460 |
| 10 | 88* | 796 | 1552 |
| 6 | 107* | 953.3 | 1840 |
| 5 | 96* | 1040 | 1960 |
| 4 | 110* | 1140 | 2120 |
| 3 | 200* | 1320* | 2400 |
| 2.5 | 160* | 1408* | 2640 |
| 2.0 | Under | 1660* | 2980 |
| 1.5 | Under | 1760* | 3440 |
| 1.0 | Under | 2200* | 4280 |
| .6 | Under | 3533* | 5867* |
| .5 | Under | 4000* | 6960* |
| .3 | Under | 4667* | 8400* |

*Outside of acceptable limits of sensitivity for Brookfield viscometer
Under: Measurement of 0.00
Over: Over maximum torque capacity of viscometer The lotion formulation containing a 1% w/v dispersion of microparticles of D,L-γ-poly(glutamate) cross-linked with the ethylene glycol diglycidyl ether had a favorable rheological profile, with favorable sensory qualities, including a non-oily and non-sticky skin sensation, and good spreadability.

What is claimed is:

1. A method of preparing a rheology modifier comprising:
    cross-linking a poly(amino acid) with a cross-linker to produce a cross-linked poly(amino acid) and simultaneously drying the cross-linked poly(amino acid) by heating a solution of the poly(amino acid) and a cross-linker in water at a temperature at which the water evaporates and the cross-linker crosslinks the poly (amino acid) to form a dried resin including the cross-linked poly(amino acid);
    dispersing the dried resin in water to rehydrate the dried resin with the cross-linked poly(amino acid); and
    grinding the rehydrated cross-linked poly(amino acid) to have a mean equivalent diameter when fully swollen in deionized water of up to about 1000 μm, as measured by laser diffraction.

2. The method of claim 1, wherein the poly(amino acid) comprises a member selected from the group consisting of amino acid homopolymers and copolymers.

3. The method of claim 1, wherein the poly(amino acid) comprises a member selected from the group consisting of D-γ-poly(glutamic acid), L-γ-poly(glutamic acid), D,L-γ-poly(glutamic acid), and combinations thereof.

4. The method of claim 1, wherein the cross-linked poly(amino acid) has a cross-link density of from one cross-link bond per ten monomer units up to one cross-link bond per about 100,000 monomer units.

5. The method of claim 1, wherein the cross-linker comprises a plurality of reactive functional groups selected from the group consisting of epoxide groups, aziridine groups; and carbodiimide groups; wherein, when the cross-linker comprises carbodiimide groups, the solution further comprises an amine compound having a plurality of reactive amine groups.

* * * * *